United States Patent
Kim et al.

(10) Patent No.: US 12,226,757 B2
(45) Date of Patent: Feb. 18, 2025

(54) AMMOXIDATION CATALYST FOR PROPYLENE, MANUFACTURING METHOD OF THE SAME CATALYST, AMMOXIDATION METHOD USING THE SAME CATALYST

(71) Applicant: LG CHEM, LTD., Seoul (KR)

(72) Inventors: Ji Yeon Kim, Daejeon (KR); Kyungyeon Kang, Daejeon (KR); Jun Seon Choi, Daejeon (KR)

(73) Assignee: LG CHEM, LTD., Seoul (KR)

( * ) Notice: Subject to any disclaimer, the term of this patent is extended or adjusted under 35 U.S.C. 154(b) by 775 days.

(21) Appl. No.: 17/291,558

(22) PCT Filed: Sep. 25, 2020

(86) PCT No.: PCT/KR2020/013099
§ 371 (c)(1),
(2) Date: May 5, 2021

(87) PCT Pub. No.: WO2021/066411
PCT Pub. Date: Apr. 8, 2021

(65) Prior Publication Data
US 2022/0001361 A1 Jan. 6, 2022

(30) Foreign Application Priority Data

Sep. 30, 2019 (KR) .................. 10-2019-0121172
Sep. 24, 2020 (KR) .................. 10-2020-0124245

(51) Int. Cl.
*B01J 21/08* (2006.01)
*B01J 23/00* (2006.01)
(Continued)

(52) U.S. Cl.
CPC ......... *B01J 23/8872* (2013.01); *B01J 23/002* (2013.01); *B01J 35/397* (2024.01);
(Continued)

(58) Field of Classification Search
CPC .......... B01J 21/08; B01J 23/002; B01J 23/02; B01J 23/04; B01J 23/18; B01J 23/22;
(Continued)

(56) References Cited

U.S. PATENT DOCUMENTS 3,766,092 A 10/1973 Hirakawa et al.
4,052,332 A 10/1977 D'Amore et al.
(Continued)

FOREIGN PATENT DOCUMENTS

CA 805705 A 2/1969
CN 1744949 A 3/2006
(Continued)

OTHER PUBLICATIONS

Binh et al., "Ammoxidation of Acrolein to Acrylonitrile Over Bismuth Molybdate Catalysts", Applied Catalysis a General, vol. 520 (2016), pp. 7-12.
(Continued)

*Primary Examiner* — Cam N. Nguyen
(74) *Attorney, Agent, or Firm* — BRYAN CAVE LEIGHTON PAISNER LLP

(57) ABSTRACT

An ammoxidation catalyst includes a metal oxide represented by Chemical Formula 1, wherein a first peak having intensity of A appears in the 2θ range of 26.3±0.5°, and a second peak having intensity of B appears in the 2θ range of 28.3±0.5° in X ray diffraction analysis by CuKα, and an intensity ratio (A/B) of the first peak to the second peak is 1.5 or more:

$$Mo_xBi_aFe_bA_cB_dC_eD_fO_y \quad \text{Chemical Formula 1}$$

wherein in Chemical Formula 1,
A and B are different from each other, and each independently, are one or more elements of Ni, Mn, Co, Zn, Mg, Ca, and Ba,
C is one or more elements of Li, Na, K, Rb, and Cs,
(Continued)

D is one or more elements of Cr, W, B, Al, Ca, and V,
a to f, x, and y are respectively mole fractions of each atom or atomic group,
a is 0.1 to 7, b is 0.1 to 7, provided that the sum of a and b is 0.1 to 7,
c is 0.1 to 10, d is 0.01 to 5, e is 0.1 to 10, f is 0 to 10,
x is 11 to 14, y is a value determined by each oxidation number of Mo, Bi, Fe, A, B, C, and D.

20 Claims, 3 Drawing Sheets

(51) Int. Cl.

| | | |
|---|---|---|
| B01J 23/02 | (2006.01) | |
| B01J 23/04 | (2006.01) | |
| B01J 23/18 | (2006.01) | |
| B01J 23/22 | (2006.01) | |
| B01J 23/26 | (2006.01) | |
| B01J 23/28 | (2006.01) | |
| B01J 23/30 | (2006.01) | |
| B01J 23/31 | (2006.01) | |
| B01J 23/34 | (2006.01) | |
| B01J 23/74 | (2006.01) | |
| B01J 23/745 | (2006.01) | |
| B01J 23/75 | (2006.01) | |
| B01J 23/755 | (2006.01) | |
| B01J 23/78 | (2006.01) | |
| B01J 23/84 | (2006.01) | |
| B01J 23/843 | (2006.01) | |
| B01J 23/847 | (2006.01) | |
| B01J 23/85 | (2006.01) | |
| B01J 23/88 | (2006.01) | |
| B01J 23/881 | (2006.01) | |
| B01J 23/887 | (2006.01) | |
| B01J 35/10 | (2006.01) | |
| B01J 35/30 | (2024.01) | |
| B01J 35/61 | (2024.01) | |
| B01J 35/63 | (2024.01) | |
| B01J 37/02 | (2006.01) | |
| B01J 37/04 | (2006.01) | |
| B01J 37/08 | (2006.01) | |

(52) U.S. Cl.
CPC ........... *B01J 35/613* (2024.01); *B01J 35/615* (2024.01); *B01J 35/633* (2024.01); *B01J 35/635* (2024.01); *B01J 35/638* (2024.01); *B01J 37/0201* (2013.01); *B01J 37/04* (2013.01); *B01J 37/08* (2013.01)

(58) Field of Classification Search
CPC ........... B01J 23/26; B01J 23/28; B01J 23/30; B01J 23/31; B01J 23/34; B01J 23/74; B01J 23/745; B01J 23/75; B01J 23/755; B01J 23/78; B01J 23/84; B01J 23/8437; B01J 23/8472; B01J 23/85; B01J 23/88; B01J 23/881; B01J 23/8872; B01J 23/8876; B01J 35/1014; B01J 35/1019; B01J 35/1042; B01J 35/1047; B01J 35/1061; B01J 37/0209; B01J 37/04; B01J 37/08
See application file for complete search history.

(56) References Cited

U.S. PATENT DOCUMENTS

| | | | |
|---|---|---|---|
| 4,123,453 A | 10/1978 | Grasselli et al. | |
| 4,156,660 A | 5/1979 | Grasselli et al. | |
| 4,176,234 A | 11/1979 | Grasselli et al. | |
| 4,182,907 A | 1/1980 | Grasselli et al. | |
| 4,259,211 A | 3/1981 | Krabetz et al. | |
| 4,264,476 A | 4/1981 | Umemura et al. | |
| 4,280,929 A | 7/1981 | Shaw et al. | |
| 4,290,922 A | 9/1981 | Umemura et al. | |
| 4,298,763 A | 11/1981 | Engelbach et al. | |
| 4,374,759 A | 2/1983 | Khoobiar | |
| 4,382,880 A | 5/1983 | Derrien | |
| 4,388,223 A | 6/1983 | Ferlazzo et al. | |
| 4,388,226 A | 6/1983 | Derrien et al. | |
| 4,418,007 A | 11/1983 | Derrien | |
| 4,479,013 A | 10/1984 | Khoobiar | |
| 4,503,001 A | 3/1985 | Grasselli et al. | |
| 4,541,964 A | 9/1985 | Katsumata et al. | |
| 4,590,173 A | 5/1986 | Sasaki et al. | |
| 4,609,635 A | 9/1986 | Canavesi et al. | |
| 4,767,878 A | 8/1988 | Grasselli et al. | |
| 4,863,891 A | 9/1989 | Grasselli et al. | |
| 5,093,299 A * | 3/1992 | Suresh | C07C 253/26 502/215 |
| 5,175,334 A | 12/1992 | Suresh et al. | |
| 5,212,137 A * | 5/1993 | Suresh | B01J 23/8878 502/215 |
| 5,602,280 A * | 2/1997 | Nagai | B01J 27/192 562/599 |
| 5,658,842 A * | 8/1997 | Midorikawa | B01J 23/8876 502/316 |
| 5,663,113 A * | 9/1997 | Midorikawa | B01J 23/8876 502/316 |
| 5,728,894 A | 3/1998 | Nagano et al. | |
| 5,780,664 A | 7/1998 | Aoki | |
| 6,143,690 A | 11/2000 | Komada et al. | |
| 6,245,931 B1 | 6/2001 | Aoki et al. | |
| 6,458,742 B1 | 10/2002 | Paparizos et al. | |
| 6,509,508 B2 | 1/2003 | Kimura et al. | |
| 6,525,217 B1 | 2/2003 | Unverricht et al. | |
| 6,545,177 B2 | 4/2003 | Tanimoto et al. | |
| 6,723,869 B1 | 4/2004 | Mori et al. | |
| 6,781,013 B2 | 8/2004 | Tanimoto | |
| 6,784,134 B2 | 8/2004 | Kasuga et al. | |
| 6,797,839 B1 | 9/2004 | Hibst et al. | |
| 6,818,702 B1 | 11/2004 | Orikabe et al. | |
| 6,878,847 B2 | 4/2005 | Kasuga et al. | |
| 6,888,024 B2 | 5/2005 | Dieterle et al. | |
| 6,921,836 B1 | 7/2005 | Hibst et al. | |
| 6,965,046 B2 | 11/2005 | Paparizos et al. | |
| 7,071,140 B2 * | 7/2006 | Paparizos | C07C 253/26 558/321 |
| 7,348,291 B2 | 3/2008 | Paparizos et al. | |
| 7,365,041 B2 | 4/2008 | Miyaki et al. | |
| 7,473,666 B2 * | 1/2009 | Yanagi | B01J 23/8876 558/321 |
| 7,635,786 B2 | 2/2009 | Shin et al. | |
| 7,579,501 B2 * | 8/2009 | Teshigahara | B01J 35/1038 562/545 |
| 7,632,777 B2 * | 12/2009 | Teshigahara | C07C 45/34 502/316 |
| 7,638,458 B2 | 12/2009 | Shin et al. | |
| 7,649,111 B2 | 1/2010 | Liang et al. | |
| 7,732,367 B2 | 6/2010 | Stevenson et al. | |
| 7,943,710 B2 | 5/2011 | Shin et al. | |
| 7,999,133 B2 | 8/2011 | Stevenson et al. | |
| 8,153,546 B2 * | 4/2012 | Brazdil | B01J 35/002 502/243 |
| 8,247,344 B2 | 8/2012 | Shin et al. | |
| 8,258,073 B2 * | 9/2012 | Besecker | B01J 35/002 558/324 |
| 8,350,075 B2 * | 1/2013 | Brazdil | B01J 23/002 558/324 |
| 8,354,482 B2 | 1/2013 | Shin et al. | |
| 8,361,923 B2 * | 1/2013 | Kano | C22B 23/026 502/313 |
| 8,420,566 B2 * | 4/2013 | Brazdil | C07C 253/26 558/324 |
| 8,455,388 B2 * | 6/2013 | Brazdil | B01J 23/8878 558/324 |

(56) References Cited

U.S. PATENT DOCUMENTS

| | | | |
|---|---|---|---|
| 8,686,194 B2* | 4/2014 | Macht | B01J 35/026 502/311 |
| 9,199,921 B2 | 12/2015 | Endo et al. | |
| 9,211,527 B1* | 12/2015 | Brazdil, Jr. | B01J 23/887 |
| 9,346,036 B2* | 5/2016 | Yoshida | B01J 35/002 |
| 9,358,528 B2* | 6/2016 | Brazdil | B01J 23/887 |
| 9,364,817 B2* | 6/2016 | Yoshida | B01J 23/8872 |
| 9,815,045 B2* | 11/2017 | Lugmair | B01J 23/8876 |
| 9,844,769 B2* | 12/2017 | Brazdil | B01J 23/8878 |
| 10,137,437 B2* | 11/2018 | Sokolovskii | B01J 23/002 |
| 10,479,759 B2* | 11/2019 | Li | B01J 35/023 |
| 10,479,760 B2* | 11/2019 | Lugmair | B01J 23/8898 |
| 10,626,082 B2* | 4/2020 | Brazdil | B01J 37/08 |
| 10,682,631 B2* | 6/2020 | Amakawa | B01J 35/1009 |
| 10,780,427 B2* | 9/2020 | Brazdil | B01J 23/8878 |
| 10,894,247 B2* | 1/2021 | Yang | B01J 37/04 |
| 10,940,463 B2* | 3/2021 | Iitsuka | B01J 37/16 |
| 11,433,383 B2* | 9/2022 | Aiki | B01J 37/088 |
| 2001/0051589 A1 | 12/2001 | Van Berge et al. | |
| 2002/0198398 A1* | 12/2002 | Paparizos | C07C 253/26 558/322 |
| 2004/0063988 A1 | 4/2004 | Hechler et al. | |
| 2005/0187406 A1 | 8/2005 | Kang et al. | |
| 2005/0245623 A1 | 11/2005 | Van Berge et al. | |
| 2006/0155139 A1 | 7/2006 | Yanagi et al. | |
| 2006/0199730 A1 | 9/2006 | Seely et al. | |
| 2010/0076208 A1 | 3/2010 | Dhingra et al. | |
| 2011/0092757 A1 | 4/2011 | Akagishi et al. | |
| 2011/0237753 A1 | 9/2011 | Brazdil et al. | |
| 2012/0130112 A1 | 5/2012 | Brazdil et al. | |
| 2013/0023699 A1 | 1/2013 | Macht et al. | |
| 2015/0238939 A1 | 8/2015 | Yoshida et al. | |
| 2015/0367329 A1 | 12/2015 | Lim et al. | |
| 2016/0051967 A1 | 2/2016 | Sokolovskii et al. | |
| 2016/0175817 A1 | 6/2016 | Brazdil et al. | |
| 2017/0114007 A1* | 4/2017 | Brazdil | B01J 23/8993 |
| 2018/0133699 A1 | 5/2018 | Brazdil et al. | |
| 2018/0222850 A1 | 8/2018 | Li et al. | |
| 2018/0222851 A1 | 8/2018 | Lugmair et al. | |
| 2018/0318803 A1* | 11/2018 | Fukuzawa | C07C 253/26 |
| 2019/0001309 A1* | 1/2019 | Fukuzawa | B01J 35/002 |
| 2019/0076829 A1* | 3/2019 | Sprenger | B01J 27/057 |
| 2021/0070693 A1 | 3/2021 | Morii et al. | |
| 2022/0001361 A1 | 1/2022 | Kim et al. | |
| 2022/0002233 A1* | 1/2022 | Kang | B01J 37/035 |
| 2022/0023837 A1* | 1/2022 | Kang | B01J 23/8876 |
| 2022/0395817 A1* | 12/2022 | Kim | B01J 37/0221 |
| 2023/0373908 A1* | 11/2023 | Ryou | C07C 253/24 |

FOREIGN PATENT DOCUMENTS

| | | | | |
|---|---|---|---|---|
| CN | 110214054 A | 9/2019 | | |
| CN | 110248730 A | 9/2019 | | |
| EP | 1 602 405 A1 * | 12/2005 | | B01J 23/88 |
| EP | 3974058 A1 | 3/2022 | | |
| JP | S47013313 U | 10/1972 | | |
| JP | S55056839 A | 4/1980 | | |
| JP | S57171437 A | 10/1982 | | |
| JP | S60-166037 A | 8/1985 | | |
| JP | H0747271 A | 2/1995 | | |
| JP | 2000037631 A | 2/2000 | | |
| JP | 2002526241 A | 8/2002 | | |
| JP | 2006521916 A | 9/2006 | | |
| JP | 2010240593 A | 10/2010 | | |
| JP | 2005313167 A | 8/2011 | | |
| JP | 2013527141 A | 6/2013 | | |
| JP | 2013-169482 A | 9/2013 | | |
| JP | 2016120468 A | 7/2016 | | |
| JP | 2016520418 A | 7/2016 | | |
| JP | 6124883 B2 | 5/2017 | | |
| JP | 2018-140326 A | 9/2018 | | |
| JP | 2022512791 A | 2/2022 | | |
| KR | 10-2005-0098270 A | 10/2005 | | |
| KR | 10-0687671 B1 | 3/2007 | | |
| KR | 10-0977358 B1 | 8/2010 | | |
| KR | 10-2012-0021858 A | 3/2012 | | |
| KR | 10-2013-007625 A | 1/2013 | | |
| KR | 10-2015-0046224 A | 4/2015 | | |
| KR | 10-1537459 B1 | 7/2015 | | |
| KR | 10-2016-0066922 A | 6/2016 | | |
| KR | 10-2016-0083698 A | 7/2016 | | |
| KR | 10-2017-0007947 A | 1/2017 | | |
| KR | 10-2017-0139602 A | 12/2017 | | |
| WO | 2004078344 A1 | 9/2004 | | |
| WO | 2011-119203 A1 | 9/2011 | | |
| WO | 2014169163 | 10/2014 | | |
| WO | 2014051090 A1 | 8/2016 | | |
| WO | 2017130909 A1 | 8/2017 | | |
| WO | 2018148158 A1 | 8/2018 | | |
| WO | 2018148240 A1 | 8/2018 | | |
| WO | 2019187786 A1 | 10/2019 | | |

OTHER PUBLICATIONS

Industrial Catalysis, Wang Wenxing et al., Beijing: Chemical Industry Press, p. 223, Dec. 1978.

* cited by examiner

AMMOXIDATION CATALYST FOR PROPYLENE, MANUFACTURING METHOD OF THE SAME CATALYST, AMMOXIDATION METHOD USING THE SAME CATALYST

The present application is a National Phase entry pursuant to 35 U.S.C. § 371 of International Application No. PCT/KR2020/013099 filed on Sep. 25, 2020, and claims priority to and the benefit of Korean Patent Application No. 10-2019-0121172 filed on Sep. 30, 2019, and Korean Patent Application No. 10-2020-0124245 filed on Sep. 24, 2020 with the Korean Intellectual Property Office, the disclosures of which are herein incorporated by reference in their entirety.

FIELD

This invention relates to an ammoxidation catalyst for propylene, a manufacturing method of the same, and an ammoxidation method using the same.

BACKGROUND

An ammoxidation process of propylene is based on a mechanism of reduction in which ammonia and propylene are reacted and reoxidized, and in order to increase conversion of the reactant (namely, propylene) and selectivity and yield of the reaction product (namely acrylonitrile), catalysts of various compositions have been studied.

Specifically, since a Mo (molybdenum)-Bi (bismuth) oxide catalyst has been suggested, in order to increase the catalytic activity and stability, catalysts to which metals of various oxidation states are added have been studied. As the result, the yield of acrylonitrile was improved compared to the initial studies, according to the kind or amount of added metals.

However, despite diversification of catalyst compositions, due to insufficient studies on the structure and properties, remarkable increase in the conversion of the reactant (namely, propylene) and selectivity of the reaction product (namely, acrylonitrile) during the ammoxidation of propylene was limited.

Specifically, in general, metal precursors of aimed compositions and nano silica sol are coprecipitated, and then, spray dried and calcined, thus obtaining a catalyst of a secondary particle structure in which metal oxide particles and silica particles are agglomerated.

However, the catalyst having the secondary particle structure inevitably has high crystallinity while passing through spray drying during the manufacturing process. The catalyst having high crystallinity may be easily cracked or broken by high temperature, and Mo, and the like may exhibit dissolution from the inside to the surface, and thus, the catalytic performance may be degraded.

It is an object of the invention to provide an ammoxidation catalyst for propylene in which Mo dissolution is inhibited during ammoxidation of propylene, and catalytic activity is maintained high.

SUMMARY

Specifically, according to one embodiment of the invention, there is provided an ammoxidation catalyst for propylene that not only exhibits high activity to ammoxidation of propylene, but also has high amorphous phase content.

Since the ammoxidation catalyst for propylene not only exhibits high activity to ammoxidation of propylene, but also has high amorphous phase content, Mo dissolution is inhibited during ammoxidation of propylene, and catalytic activity may be maintained at a high level.

Thus, using the catalyst of one embodiment, propylene can be converted at higher rate, and acrylonitrile can be prepared with higher yield.

DETAILED DESCRIPTION

Figure 1:
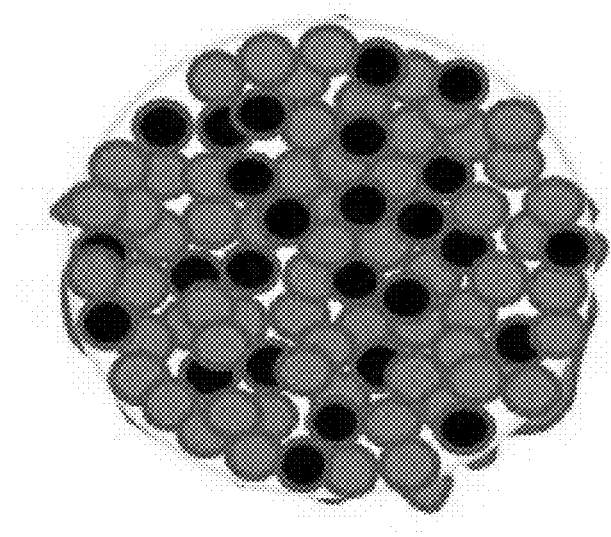
FIG. 1 is a schematic illustration showing the catalyst prepared using spray drying.

Although various modifications can be made to the invention and the invention may have various forms, specific examples will be illustrated and explained in detail below. However, it should be understood that these are not intended to limit the invention to specific disclosure, and that the invention includes all modifications, equivalents or replacements thereof without departing from the spirit and technical scope of the invention. In explanation of the invention, in case it is judged that specific explanations regarding related known technologies may obscure the subject matter of the invention, those explanations will be omitted.

And, terms including ordinal numbers such as "a first", "a second" and the like are used to explain various constructional elements, but the constructional elements are not limited by these terms. These terms are used only to distinguish one constructional element from other constructional elements. For example, the first constructional element may be named as the second constructional element, and similarly, the second constructional elements may be also named as the first constructional elements, without departing from the scope of the right of the invention.

A singular expression includes a plural expression thereof, unless it is expressly stated or obvious from the context that such is not intended. As used herein, the terms "comprise" or "have", etc. are intended to designate the existence of practiced characteristic, number, step, constructional element or combinations thereof, and they are not intended to preclude the possibility of existence or addition of one or more other characteristics, numbers, steps, constructional elements or combinations thereof.

Hereinafter, an ammoxidation catalyst for propylene according to one embodiment will be explained in detail with reference to drawings.

An Ammoxidation Catalyst for Propylene

According to one embodiment of the invention, there is provided an ammoxidation catalyst for propylene comprising metal oxide represented by Chemical Formula 1,
wherein a first peak having intensity of A appears in the 2θ range of 26.3±0.5°, and a second peak having intensity of B appears in the 2θ range of 28.3±0.5° in X ray diffraction analysis by CuKα, and
a intensity ratio (A/B) of the first peak to the second peak is 1.5 or more:

$$Mo_xBi_aFe_bA_cB_dC_eD_fO_y \quad \text{Chemical Formula 1}$$

in the Chemical Formula 1,

A and B are different from each other, and each independently, are one or more elements of Ni, Mn, Co, Zn, Mg, Ca, and Ba, C is one or more elements of Li, Na, K, Rb, and Cs, D is one or more elements of Cr, W, B, Al, Ca, and V, a to f, x, and y are respectively mole fractions of each atom or atomic group, a is 0.1 to 7, b is 0.1 to 7, provided that the sum of a and b is 0.1 to 7, c is 0.1 to 10, d is 0.01 to 5, e is 0.1 to 10, f is 0 to 10, x is 11 to 14, y is a value determined by each oxidation number of Mo, Bi, Fe, A, B, C, and D.

As mentioned above, as the ammoxidation catalyst for propylene, catalysts having a secondary particle structure prepared through coprecipitation of metal precursors and nano silica sol and spray drying are known.

In the catalyst having a secondary particle structure, metal oxide particles are uniformly distributed inside and outside, but pores are scarcely included, and thus, adsorption amount of reactants per unit volume is small and reaction activity is low.

Meanwhile, the catalyst having a secondary particle structure inevitably has high crystallinity while passing through spray drying during the manufacturing process. A catalyst having high crystallinity may be easily cracked or broken by high temperature, and Mo and the like may exhibit dissolution from the inside to the surface, and thus, catalytic performance may be degraded.

On the contrary, a catalyst of one embodiment not only exhibits high activity to ammoxidation of propylene, but also has high amorphous phase content, and thus, dissolution of Mo is inhibited during ammoxidation of propylene, and catalytic activity may be maintained high.

Wherein, the amorphous phase exhibiting high activity to ammoxidation of propylene may be a complex oxide phase of molybdenum (Mo) and heterogeneous metals, for example, a $CoMoO_4$ phase.

Specifically, in X ray diffraction (XRD) analysis of the catalyst of one embodiment, a first peak having intensity of B may appear in the 2θ range of 26.3±0.5°, and a second peak having intensity of A may appear in the 2θ range of 28.3±0.5°.

Wherein, the first peak may appear due to a complex oxide phase of molybdenum (Mo) and heterogeneous metals, for example, a $CoMoO_4$ phase. And, the second peak may appear due to a molybdenum (Mo) oxide phase, for example, a $MoO_3$ phase.

The complex oxide phase of molybdenum (Mo) and heterogeneous metals exhibits activity to ammoxidation of propylene, while the $MoO_3$ phase does not exhibit activity to ammoxidation of propylene.

The catalyst of a secondary particle structure is prepared from a slurry in which silica sol and metal oxide precursors are non-uniformly mixed, has relatively high content of a $MoO_3$ phase, which is an inactive phase, and has a intensity ratio (A/B) of the first peak to the second peak less than 1.5. Thus, during ammoxidation of propylene, Mo dissolution is generated, and catalytic activity may be degraded.

On the contrary, the catalyst of one embodiment has relatively high content of complex oxide phase of heterogeneous metals, which is an active phase, has a intensity ratio (A/B) of the first peak to the second peak of 1.5 or more, specifically 2.0 or more, more specifically 2.5 or more, for example 3.0 or more.

Although more detailed explanations will be made later, the catalyst of one embodiment may be prepared using impregnation. If a very uniform transparent solution is supported on silica, metal components may be sufficiently bonded to each other, and thus, a probability of forming a $MoO_3$ phase alone may become very low.

Particularly, since the wide surface area of a carrier itself is utilized, dispersibility of active phases such as $FeMoO_3$, $Bi_2MoO_6$, as well as $CoMoO_4$, may be much improved. Although XRD peak intensity tends to decrease if dispersibility is improved, the amount of Mo and Co added to form metal oxide is large in one embodiment, an XRD pattern may be formed wherein the $CoMoO_4$ peak is significantly developed.

Thus, the catalyst of one embodiment may maintain high catalytic activity while Mo dissolution is inhibited during ammoxidation of propylene, compared to the catalyst of a secondary particle structure.

Meanwhile, in the case of a catalyst that does not include heterogeneous metals other than Bi, for example, a catalyst comprising Mo and Bi only as metal components, a complex oxide phase of Mo and heterogeneous metals may not be formed, and thus, the first peak may not appear in XRD analysis.

Namely, since a catalyst that does not include heterogeneous metals other than Bi comprises only a $MoO_3$ phase, which is an inactive phase and crystalline, Mo dissolution is generated during ammoxidation of propylene, and catalytic activity may be degraded.

Hereinafter, the catalyst of one embodiment will be explained in detail.

D50 Particle Diameter, Pore Volume and BET Specific Surface Area of a Catalyst

Since the catalyst of one embodiment comprises many pores having large volumes, it may provide an effective surface area in which pores as well as external surface area can participate in reactions.

Specifically, the catalyst of one embodiment may have D50 particle diameter of 10 to 300 μm, comprise pores having a volume of 0.3 to 1.3 $cm^3/g$, and have BET specific surface area of 50 to 300 $m^2/g$.

The BET specific surface area and pore volume provided by the catalyst of one embodiment are improved compared to the catalyst of a secondary particle structure, and thus, it can convert propylene with higher rate, and obtain acrylonitrile with higher selectivity and yield.

Within the above ranges, as the pore volume included in the catalyst of one embodiment increases, the BET specific surface area of a catalyst including the same may also increase. However, if the pore volume included in the catalyst of one embodiment excessively increases, the content of metal oxides may relatively decrease, and thus, catalytic activity may decrease.

Thus, generally considering the desired of the catalyst of one embodiment, the BET specific surface area and pore volume, and the like may be controlled.

For example, D50 particle diameter of the catalyst of one embodiment may be controlled to 10 μm or more, 20 μm or more, 30 μm or more, or 45 μm or more, and 300 μm or less, 280 μm or less, 260 μm or less, 240 μm or less, 220 μm or less, or 200 μm or less.

And, the pore volume of the catalyst of one embodiment may be controlled to 0.3 $cm^3/g$ or more, 0.35 $cm^3/g$ or more, 0.4 $cm^3/g$ or more, 0.45 $cm^3/g$ or more, or 0.5 $cm^3/g$ or more, and 1.3 $cm^3/g$ or less, 1.2 $cm^3/g$ or less, 1.1 $cm^3/g$ or less, 1.0 $cm^3/g$ or less.

And, the catalyst of one embodiment may have BET specific surface area of 50 $m^2/g$ or more, 70 $m^2/g$ or more, 90 $m^2/g$ or more, 110 m²/g or more, or 120 m²/g or more, and 300 m²/g or less, 270 m²/g or less, 240 m²/g or less, 210 m²/g or less, or 180 m²/g or less.

Metal Oxide

Meanwhile, even if a catalyst has the same structure as the catalyst of one embodiment, if the kind and content of the components constituting the metal oxide do not satisfy Chemical Formula 1, active sites formed may be insufficient for propylene ammoxidation or have excessively high density.

Thus, the kind and content of the components constituting the metal oxide should satisfy Chemical Formula 1. For example, the metal oxide may be represented by Chemical Formula 1-1, and due to the synergistic effect of the metal components included therein, it may be favorable for increasing active sites for ammoxidation of propylene:

  Chemical Formula 1-1

In the Chemical Formula 1-1, x, a to e and y are as defined above.

The composition and content of the metal oxide may be directly measured using measuring apparatus such as ICP (Inductively Coupled Plasma).

Structure of a Catalyst

As explained above, commonly known propylene ammoxidation catalysts are prepared by coprecipitation and spray drying, and provided as a secondary particle structure in which metal oxide nanoparticles and silica nanoparticles are agglomerated (FIG. 1).

Figure 2:
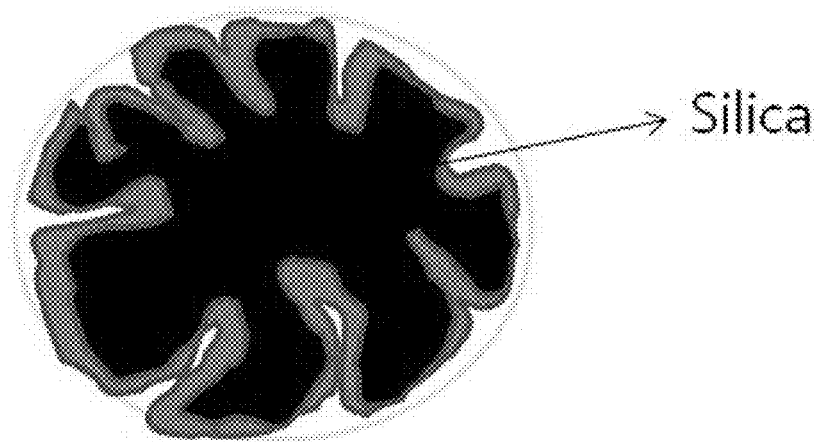
FIG. 2 is a schematic illustration showing the catalyst according to one embodiment.

Since metal oxide particles are uniformly distributed inside and outside, but parts capable of participating in propylene ammoxidation reactions are limited to the external surface parts (namely, the surfaces of secondary particles), and a small surface area is provided, the amount of ammonia detached from the catalyst surface during the propylene ammoxidation reaction is large. On the contrary, since the catalyst of one embodiment is prepared by impregnation, it may be provided as a structure wherein metal oxide is supported on a silica carrier (FIG. 2).

For example, a silica carrier may be impregnated with a metal precursor solution by immersing the silica carrier in the metal precursor solution prepared such that a desired stoichiometric molar ratio of metal oxide is satisfied.

Thereafter, if a solvent (namely, water) is removed by drying, the metal precursor may remain on the pore walls of the silica carrier, and the metal precursor may be oxidized during a calcination process to form a film continuously coating the pore walls of the silica carrier.

The catalyst of one embodiment thus prepared may further comprise a silica carrier supporting the metal oxide.

In this case, the catalyst of one embodiment may have a structure comprising a silica carrier comprising second pores; an internal coating layer that continuously coats the wall surfaces of the second pores, and comprises metal oxide represented by Chemical Formula 1; and first pores positioned inside of the second pores, and occupying empty spaces except the internal coating layer.

A catalyst having the above structure, even if a classification process is not performed as post treatment after preparation, may have better durability than a catalyst prepared with the same composition by coprecipitation and spray drying.

And, by uniformly supporting the metal oxide on the internal pores of the silica carrier, parts capable of participating in a propylene ammoxidation reaction may be extended to the internal surfaces (pores) as well as to the external surface parts (namely, the surface of the catalyst).

Specifically, the catalyst of one embodiment may have an egg-shell structure.

For this purpose, a silica carrier comprising a non-porous core part; and a porous shell part positioned on the surface of the non-porous core, and comprising second pores; may be used.

More specifically, the porous shell comprises depressed parts and protruded parts of the surface, wherein the depressed parts may be formed by opening of the second pores toward the surface of the porous shell.

Thus, the catalyst of one embodiment may have a structure comprising a coating layer that continuously coats the depressed and protruded parts of the porous shell, and comprises metal oxide represented by Chemical Formula 1; and first pores occupying empty spaces except the coating layer, in the depressed parts of the silica carrier.

The structure of the catalyst of one embodiment may be confirmed through an electron microscope such as Scanning Electron Microscope (SEM).

Weight Ratio of Metal Oxide:Silica Carrier

The catalyst of one embodiment, when further comprising the silica carrier, may comprise the metal oxide and the silica carrier at a weight ratio of 10:90 to 15:95, specifically 20:80 to 50:50, for example 15:85 to 35:65 (metal oxide:silica carrier).

Within this range, the catalyst of one embodiment may have high activity and high selectivity of acrylonitrile.

The weight ratio of the metal oxide and the silica carrier may be directly measured using measurement apparatus such as ICP (Inductively Coupled Plasma).

A Method for Preparing an Ammoxidation Catalyst for Propylene

According to another embodiment of the invention, there is provided a method for preparing an ammoxidation catalyst for propylene comprising the steps of:

preparing a first precursor solution comprising a Mo precursor, preparing a second precursor solution comprising a Fe precursor; and one or more elements Ni, Mn, Co, Zn, Mg, Ca, and Ba, preparing a third precursor solution comprising a Bi precursor; a precursor of one or more elements of Ni, Mn, Co, Zn, Mg, Ca, and Ba, different from the second precursor solution; and a precursor of one or more elements of Li, Na, K, Rb, and Cs, mixing the first to third precursor solutions such that the molar ratio of metals satisfies stoichiometric mole ratio of Chemical Formula 1, supporting the mixture of the first to third precursor solutions on a silica carrier, drying the silica carrier in which the mixture of the first to third precursor solutions is supported, and calcining the dried material:

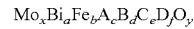  Chemical Formula 1 in the Chemical Formula 1, x, a to f and y are as defined above.

The preparation method of one embodiment corresponds to a method for preparing the catalyst of one embodiment using impregnation. Hereinafter, the preparation method of one embodiment will be explained according to each step, with the explanations overlapped being omitted.

A Preparation Process of the First Precursor Solution

The step of preparing a first precursor solution may comprise dissolving a Mo precursor in water at 50 to 90° C. to prepare an aqueous solution comprising water and a Mo precursor.

In the step of preparing the first precursor solution, additives including citric acid, oxalic acid, or a mixture thereof may be used.

In the catalyst preparation processes using coprecipitation and spray drying, these additives function as a strength control agent. While in the above one embodiment, these additives function for making the first precursor solution transparent, enabling preparation of completely dissolved precursor mixture.

When adding the additives, the weight ratio of the molybdenum precursor and the additives may be controlled to satisfy a ratio of 1:0.1 to 1:1, specifically 1:0.2 to 1:0.7, and within this range, solubility of the molybdenum precursor may be increased, but it is not limited thereto.

A Preparation Process of the Second Precursor Solution

The step of preparing the second precursor solution may comprise dissolving a Fe precursor; and a second precursor comprising one or more elements of Ni, Mn, Co, Zn, Mg, Ca, and Ba in water at 20 to 50° C. Optionally, a precursor further comprising a D precursor ((D=one or more elements of Cr, W, B, Al, Ca, and V) may be dissolved.

Wherein, considering the desired composition of metal oxide in the catalyst, the kind and amount of metal precursors may be selected.

For example, considering the composition of metal oxide satisfying Chemical Formula 1-1, an aqueous solution comprising water, a Fe precursor, and a Co precursor may be prepared.

A Preparation Process of the Third Precursor Solution

The step of preparing the third precursor solution may comprise dissolving a Bi precursor; a precursor of one or more elements of Ni, Mn, Co, Zn, Mg, Ca, and Ba, different from the second precursor solution; and a precursor of one or more elements of Li, Na, K, Rb, and Cs, in nitric acid at 20 to 50° C.

Wherein, considering the desired composition of metal oxide in the catalyst, the kind and amount of metal precursors may be selected.

For example, considering the composition of metal oxide satisfying Chemical Formula 1-1, a solution comprising a Bi precursor, a Ni precursor and a K precursor may be prepared.

A Process of Mixing Precursor Solutions

The process of preparing the first to third precursor solutions are independent from each other, and the preparation sequence is not limited.

However, considering the properties of each metal, the step of mixing the first to third precursor solutions may comprise the steps of mixing the second and the third precursor solutions, and adding the mixture of the second and the third precursor solutions dropwise to the first precursor solution.

And, when mixing the first to third precursor solutions, the mixing ratio may be controlled such that the molar ratio of metals meets the stoichiometric molar ratio of Chemical Formula 1, specifically Chemical Formula 1-1.

A Process for Supporting the Precursor Mixture Solution

After mixing the first to third precursor solutions, the mixture may be supported on a silica carrier.

Wherein, silica ($SiO_2$) particles having particle size of 10~200 μm, pore size of 20~25 nm, pore volume according to nitrogen adsorption of 1~3 $cm^3/g$, and BET specific surface area of 250~300 $m^2/g$ may be introduced in the mixture of the first to third precursor solutions and mixed, so that the mixture of the first to third precursor solutions may be supported on the pores of the silica carrier.

Specifically, the step of supporting the mixture of the first to third precursor solutions in the silica carrier comprises the steps of first mixing the silica carrier and the first to third precursor solutions at 20 to 30° C., and second mixing the first mixture at 70 to 90° C., wherein the first and second mixing time may be each independently 1 to 3 hours.

However, these conditions are no more than examples, and the conditions are not specifically limited as long as it enables sufficient supporting of the mixture of the first to third precursor solutions.

Drying and Calcinations Processes

Thereafter, the silica carrier in which the mixture of the first to third precursor solutions is supported is dried at a temperature range of 100 to 120° C. for 5 to 12 hours, and then, calcined at a temperature range of 500 to 700° C. for 1 to 6 hours, thus finally obtaining a catalyst.

However, the drying and calcinations conditions are no more than examples, and the conditions are not specifically limited as long as a solvent may be sufficiently removed from the pores of the carrier, and the metal precursors may be oxidized.

The structure of the catalyst thus formed is as explained above.

Ammoxidation Method of Propylene

According to yet another embodiment of the invention, there is provided a method for ammoxidation of propylene, comprising a step of reacting propylene and ammonia in the presence of the catalyst of the one embodiment as explained above, in a reactor.

The catalyst of one embodiment has high activity and high temperature stability, and may be used for propylene ammoxidation reaction to increase conversion of propylene and selectivity and yield of acrylonitrile.

For the details other than the catalyst of one embodiment, matters commonly known in the art may be referred to, and the detailed explanations thereof are omitted.

Hereinafter, embodiments of the invention will be explained in more detail in the following examples. However, these examples are presented only as the illustrations of the invention, and the scope of the invention is not limited thereby.

EXAMPLES

Example 1

(1) A Preparation Process of a Precursor Solution 4.24 g of a Mo precursor (($NH_4)_6Mo_7O_{24}$) was dissolved in water at 85° C., and 3 g of oxalic acid or citric acid was added thereto, thus preparing a Mo precursor solution.

Separately, 2.5 g of a Fe precursor ($Fe(NO_3)_2 \cdot 9H_2O$) and 3.5 g of a Co precursor ($Co(NO_3)_2 \cdot 6H_2O$) were dissolved in water at room temperature to prepare a mixed solution of Fe and Co precursors.

And, separately, 2 g of nitric acid was added to a mixture of 1.46 g of a Bi precursor ($Bi(NO_3)_3 \cdot 5H_2O$), 0.58 g of a Ni precursor ($Ni(NO_3)_2 \cdot 6H_2O$), and 0.2 g of a K precursor ($KNO_3$), to prepare a mixed solution of Bi, Ni, and K precursors.

After the mixed solution of Fe and Co precursors, and the mixed solution of Bi, Ni, and K precursors were mixed under stirring, it was added dropwise to the Mo precursor solution, thus obtaining a mixed solution of Mo, Bi, Fe, Ni, Co and K precursors.

In the mixed solution of precursors, the total amount of water was 45 g.

(2) A Process of Supporting Precursor Solutions in a Silica Carrier (Using Impregnation)

Silica ($SiO_2$) particles having particle size of 50-150 μm, pore size of 10-25 nm, pore volume according to nitrogen adsorption of 1~3 $cm^3/g$, and BET specific surface area of 500-600 $m^2/g$ were used as a carrier.

In the mixed solution of Mo, Bi, Fe, Ni, Co and K precursors, 13 g of the silica carrier was introduced, and stirred sequentially at room temperature and 80° C., respectively for 2 hours, so that the mixed solution of Mo, Bi, Fe, Ni, Co and K precursors was sufficiently supported in the pores of the silica carrier.

(3) A Process of Preparing a Catalyst in which Metal Oxide is Supported in a Silica Carrier And then, the silica carrier on which the mixed solution of Mo, Bi, Fe, Ni, Co and K precursors is supported was recovered and dried in an oven at 110° C. for 12 hours, and then, heat treated for 6 hours in a tubular calcinations furnace of nitrogen atmosphere, while maintaining a temperature of 580° C., thus obtaining a catalyst of Example 1 in which 25 wt % of metal oxide (mole fraction of Mo in the metal oxide is 12) is supported.

(4) An Ammoxidation Process of Propylene

In a reactor charged with 0.05 g of quartz wool for activation of a catalyst, 0.2 g of the catalyst of Example 1 was charged.

The internal pressure of the reactor charged with quartz wool and catalyst was maintained at atmospheric pressure (1 atm), and while raising the internal temperature of the reactor by 5° C./min, nitrogen and ammonia gas were flowed as pretreatment. Thereby, the internal temperature of the reactor was allowed to reach 400° C. at which an ammoxidation reaction can be carried out, so as to achieve sufficient pretreatment.

While supplying air together with reactants of propylene and ammonia in the pretreated reactor, an ammoxidation process of propylene was conducted. Wherein, the amount of the reactants supplied was such that a volume ratio propylene:ammonia:air=1:1.1:2=1.5~1:4:3, and the total weight hourly space velocity (WHSV) of propylene, ammonia and air is 1 $h^{-1}$.

After the ammoxidation reaction was completed, the product was recovered, and in order to confirm whether acrylonitrile was sufficiently produced, it was analyzed using various apparatuses.

The analysis method, analysis results, and the like will be explained in detail in Experimental Examples below.

Examples 2 to 4

(1) A Preparation Process of a Catalyst (Using Impregnation)

Each catalyst of Examples 2 to 4 was prepared by the same method as Example 1, except that a precursor solution was prepared according to the composition described in Table 1, and a silica carrier described in Table 2 was used.

(2) An Ammoxidation Process of Propylene

An ammoxidation process of propylene was conducted using each catalyst of Examples 2 to 4 instead of Example 1, and then, the product was recovered, and analyzed by the same method as Example 1.

Comparative Example 1

(1) A Preparation Process of a Catalyst (Coprecipitation and Spray Drying)

First, 200 g of a Mo precursor (Ammonium Molybdate) was dissolved in 200 g of water at 85° C., and 270 g of silica sol was added thereto and stirred, and then, the mixture was heated to about 50° C. to prepare a solution A.

Separately, to a mixture of 69.4 g of a Bi precursor ($Bi(NO_3)_3 \cdot 5H_2O$), 165 g of a Co precursor ($Co(NO_3)_2 \cdot 6H_2O$), 115 g of a Fe precursor ($Fe(NO_3)_2 \cdot 9H_2O$), 10 g of a Ni precursor ($Ni(NO_3)_2 \cdot 6H_2O$), and 17.5 g of a K precursor ($KNO_3$), 10 g of nitric acid was added, and the mixture was heated to 50° C. to prepare a solution B.

The solutions A and B were mixed under stirring to obtain an aqueous slurry, and the aqueous mixed slurry of the solutions A and B was dried at 150° C., using a rotary nozzle spray dryer. The dried product of a solid phase thus obtained was calcined at 580° C. for 3 hours to finally obtain a catalyst of Comparative Example 1.

(2) An Ammoxidation Process of Propylene

An ammoxidation process of propylene was conducted by the same method as Example 1, except that the catalyst of Comparative Example 1 was used instead of the catalyst of Example 1.

After the ammoxidation reaction of Comparative Example 1 was finished, the product was recovered, and analyzed by the same method as Example 1.

Comparative Example 2

(1) A Preparation Process of a Catalyst (Impregnation)

A catalyst of Comparative Example 2 was prepared by the same method as Example 1, except that a precursor solution was prepared according to the composition described in Table 1, and a silica carrier described in Table 2 was used.

(2) An Ammoxidation Process of Propylene

An ammoxidation process of propylene was conducted using the catalyst of Comparative Example 2 instead of the catalyst of Example 1, and then, the product was recovered and analyzed by the same method as Example 1.

TABLE 1

| | Mo precursor solution | | Heterogeneous metal precursor solution | | | | | | | |
| --- | --- | --- | --- | --- | --- | --- | --- | --- | --- | --- |
| | Citric acid | Mo | Fe | Co | Bi | Ni | K | Nitric acid | water | $SiO_2$ |
| Example 1 | 3 | 4.24 | 2.5 | 3.5 | 1.46 | 0.58 | 0.2 | 2 | 45 | 13 |
| Example 2 | 3 | 4.24 | 2.5 | 3.5 | 1.46 | 0.58 | 0.2 | 2 | 45 | 11 |
| Example 3 | 3 | 4.6 | 2.5 | 3.5 | 1.46 | 0.58 | 0.2 | 2 | 45 | 11 |
| Example 4 | 3 | 4.5 | 3 | 5 | 2 | 1.3 | 0.3 | 2 | 45 | 15 |
| Comp. Ex. 1 | — | 200 | 115 | 165 | 69.4 | 10 | 17.5 | 10 | 200 | 270 (40% Silica sol) |
| Comp. Ex. 2 | 1.06 | 3.531 | — | — | 19.403 | | | 2.60 | 64.95 | 32.477 |

In the Table 1, Mo is $(NH_4)_6Mo_7O_{24}$, Bi is $Bi(NO_3)_3 \cdot 5H_2O$, Co is $Co(NO_3)_2 \cdot 6H_2O$, Fe is $Fe(NO_3)_2 \cdot 9H_2O$, Ni is $Ni(NO_3)_2 \cdot 6H_2O$, and K is $KNO_3$. And, the omitted unit is g.

Meanwhile, the input amount of raw materials of the Table 1 was calculated considering the desired composition of the following Table 2, namely, the stoichiometric molar ratio of the final metal oxide and the content of the metal oxide. The composition and content of the metal oxide of the following Table 2 may be directly measured using a measurement apparatus such as ICP (Inductively Coupled Plasma).

TABLE 2

| | Preparation method | Catalyst construction | |
|---|---|---|---|
| | | Composition and content of metal oxide | Carrier content |
| Example 1 | impregnation | $Mo_{12}Bi_{1.5}Fe_3Ni_1Co_6K_1O_y$: 25 wt % | 75 wt % |
| Example 2 | impregnation | $Mo_{12}Bi_{1.5}Fe_3Ni_1Co_6K_1O_y$: 30 wt % | 70 wt % |
| Example 3 | impregnation | $Mo_{13}Bi_{1.5}Fe_3Ni_1Co_6K_1O_y$: 30 wt % | 70 wt % |
| Example 4 | impregnation | $Mo_{12.5}Bi_2Fe_3Ni_2Co_8K_{1.3}O_y$: 25 wt % | 75 wt % |
| Comparative Example 1 | Coprecipitation | $Mo_{12}Bi_{1.5}Fe_3Ni_1Co_6K_1O_y$: 50 wt % | 50 wt % |
| Comparative Example 2 | impregnation | $Bi_2O_{3.3} \cdot MoO_3$: 25 wt % | 75 wt % |

Experimental Example 1: Catalyst Analysis

According to the following analysis method, each catalyst of Example 1 and Comparative Example 1 was analyzed.

XRD main peak intensity ratio: For each catalyst of Example 1 and Comparative Example 1, X-Ray Diffraction (XRD) analysis was performed using Cu Kα X-ray, and then, the Cu Kα X-ray analysis results were respectively shown in FIG. 3(Example 1) and FIG. 4(Comparative Example 1).

Figure 3:
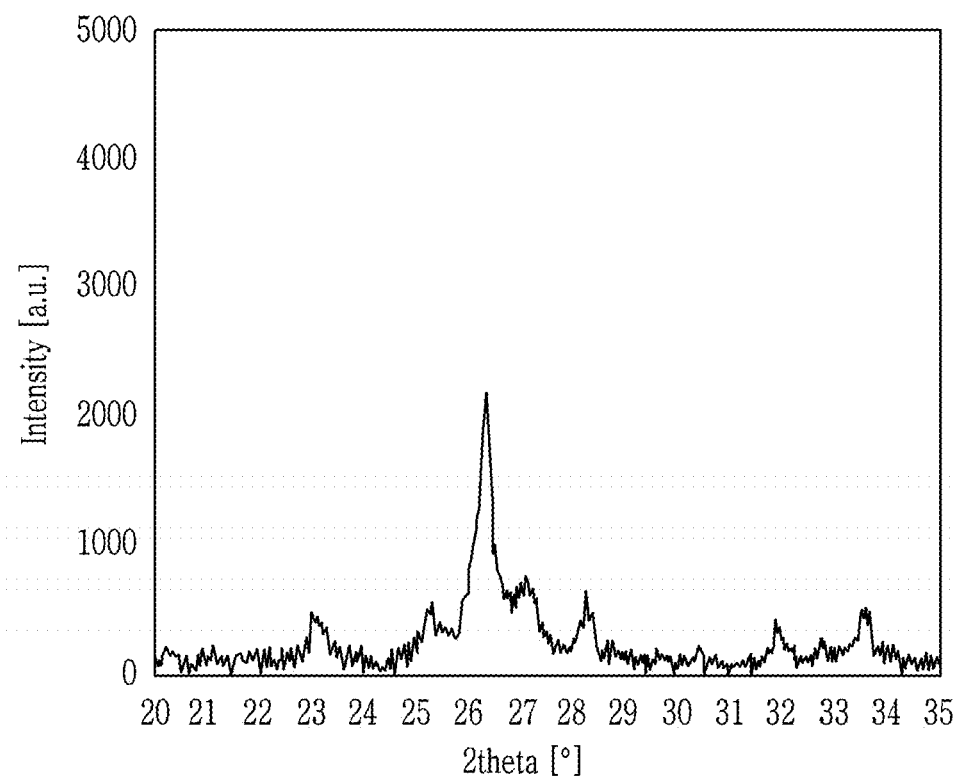
FIG. 3 shows XRD analysis results of the catalyst of one Example described below.
Figure 4:
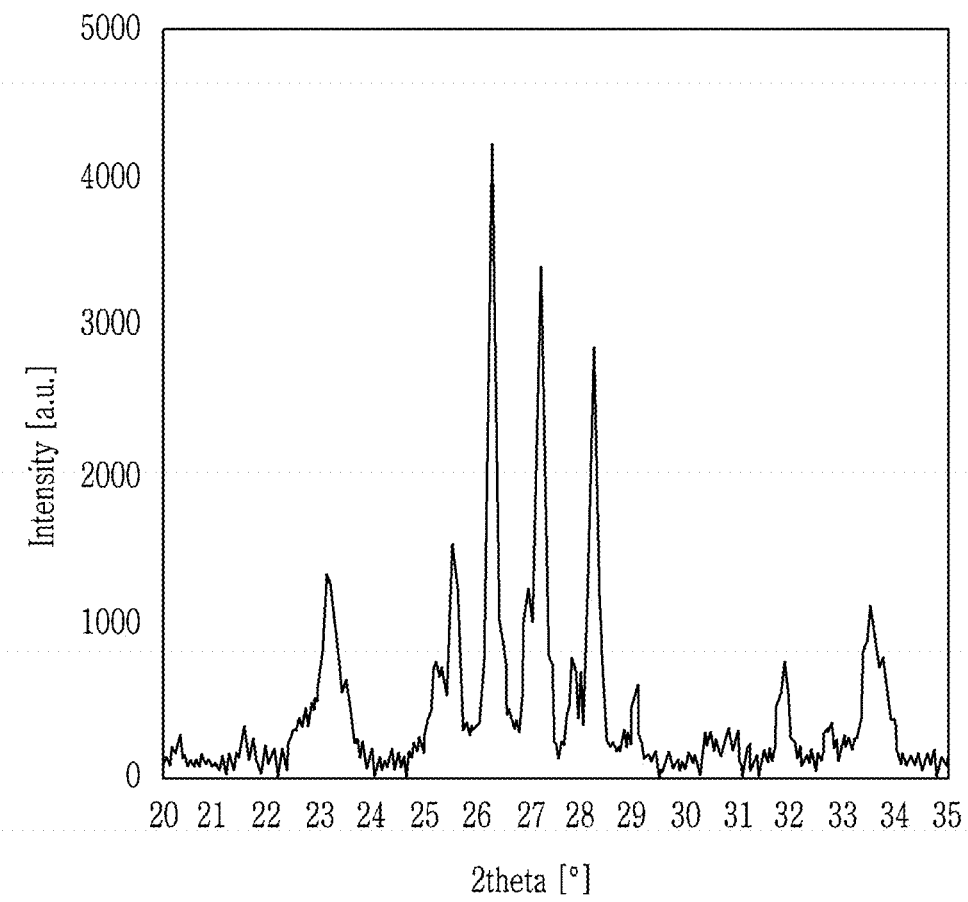
FIG. 4 shows XRD analysis results of the catalyst of one Comparative Example described below.

In FIG. 3(Example 1) and FIG. 4(Comparative Example 1), main peaks commonly appear at 26.3±0.5° and 28.3±0.5°. The intensity of the peak appeared at 26.3±0.5° was designated as A, and the intensity of the peak appeared at 28.3±0.5° was designated as B, and the peak intensity ratio of A/B was calculated for each catalyst, and the calculation values were shown in Table 3.

BET specific surface area: For each catalyst of Example 1 and Comparative Example 1, using BET specific surface area measuring device (manufacturing company: BEL Japan, device name: BELSORP-mino X), specific surface area was evaluated from nitrogen adsorption amount under liquid nitrogen temperature (77K), and the results were shown in Table 3.

Pore volume: Using a device according to ASTM D4641 (manufacturing company: BEL Japan, device name: BELSORP-mino X), pore volume in each catalyst of Example 1 and Comparative Example 1 was measured, and the results were shown in Table 3.

Catalyst structure: The structure of a catalyst may be confirmed through electron microscope such as Scanning Electron Microscope (SEM).

TABLE 3

| | Preparation method | Composition and content of metal oxide | Structure of catalyst | BET of catalyst ($m^2/g$) | Pore volume in catalyst ($cm^3/g$) | XRD A/B peak intensity ratio |
|---|---|---|---|---|---|---|
| Ex. 1 | Impreg. | $Mo_{12}Bi_{1.5}Fe_3Ni_1Co_6K_1O_y$: 25 wt % | Egg-shell | 152 | 0.86 | 5.74 |
| Ex. 2 | Impreg. | $Mo_{12}Bi_{1.5}Fe_3Ni_1Co_6K_1O_y$: 30 wt % | Egg-shell | 130 | 0.81 | 4.84 |
| Ex. 3 | Impreg. | $Mo_{13}Bi_{1.5}Fe_3Ni_1Co_6K_1O_y$: 25 wt % | Egg-shell | 125 | 0.79 | 3.36 |
| Ex. 4 | Impreg. | $Mo_{12.5}Bi_2Fe_3Ni_2Co_8K_{1.3}O_y$: 25 wt % | Egg-shell | 151.5 | 0.52 | 6.27 |
| Comp. Ex. 1 | Coprecip. | $Mo_{12}Bi_{1.5}Fe_3Ni_1Co_6K_1O_y$: 50 wt % | Uniform | 40 | 0.2 | 1.47 |
| Comp. Ex. 2 | Impreg. | $Bi_2O_{3.3} \cdot MoO_3$: 25 wt % | Egg-shell | 275 | 0.81 | (XRD peak could not be formed) |

1) Comparison of Examples 1 to 4 and Comparative Example 1

In Examples 1 to 4 and Comparative Example 1, XRD peak intensity, pore volume and BET specific surface area may be related to the preparation method of a catalyst.

Specifically, the catalyst of Comparative Example 1 has relatively many crystalline phases while passing through coprecipitation and spray drying processes, and thus, has high crystallinity.

And, the catalyst of Comparative Example 1 has a secondary particle structure that scarcely includes pores while passing through coprecipitation and spray drying processes, and thus, the effective surface area capable of participating in reaction was limited to the external surface area.

On the contrary, the catalysts of Examples 1 to 4 were prepared by impregnation, and have relatively many amorphous phases formed, and thus, have low crystallinity.

And, the catalysts of Examples 1 to 4 were prepared by impregnation and became a structure including many large pores, and thus, the effective surface area capable of participating in reaction was extended to pores.

Practically, in XRD analysis of the catalyst of Examples 1 to 4 and Comparative Example 1, a first peak having intensity of A appeared in the 2θ range of 26.3±0.5° by a $CoMoO_4$ phase, and a second peak having intensity of B appeared in the 2θ range of 28.3±0.5° by a $MoO_3$ phase.

The $CoMoO_4$ phase is an active phase for ammoxidation of propylene, and the $MoO_3$ phase is an inactive phase. Thus, it can be seen that as XRD peak intensity ratio (A/B) is higher, the crystallinity of the catalyst is lower and the activity is high.

In this regard, the catalyst of Comparative Example 1 has XRD peak intensity ratio (A/B) of just 1.47, and thus, is shown as having high crystallinity and low activity. On the contrary, the catalysts of Examples 1 to 4 meet the high range of XRD peak intensity ratio (A/B), and thus, are shown as having low crystallinity and high activity.

And, it was confirmed that compared to Comparative Example 1, the pore volumes included in the catalysts of Examples 1 to 4 are large, and the BET specific surface areas are wider.

2) Comparison of Examples 1 to 4 and Comparative Example 2

Meanwhile, in Examples 1 to 4 and Comparative Example 2, XRD peak intensity, pore volume and BET specific surface area may be related to the composition of metal oxide in the catalyst.

Specifically, although the catalyst of Comparative Example 2 was prepared by impregnation, due to the influence of metal oxide comprising Mo and Bi only, a peak by an inactive phase of $MoO_3$ was formed, and a peak by an active phase was not formed.

On the contrary, the catalysts of Examples 1 to 4 was prepared by impregnation, and the metal oxide comprise plural appropriate metal components as well as Mo and Bi, compared to the peak by an inactive phase of $MoO_3$, peak area by active phases (particularly, $CoMoO_4$) was formed wider.

And, it was assessed that in the catalysts of Examples 1 to 4, pore wall surface of the silica carrier was uniformly coated by an active phase of $CoMoO_4$, and thus, appropriate pore volume and BET specific surface area was secured.

Experimental Example 2: Analysis of Propylene Ammoxidation Product

Using Gas chromatography (Manufacturing company: Agilent Device name: HP 6890 N) equipped with FID (Flame Ionization Detector and TCD (Thermal conductivity detector), each ammoxidation product of Examples 1 to 4 and Comparative Examples 1 and 2 were analyzed.

Specifically, with FID, products including ethylene, hydrogen cyanide, acetaldehyde, acetonitrile, acrylonitrile, and the like were analyzed, and with TCD, gas products including $NH_3$, $O_2$, CO, $CO_2$, and the like were analyzed, thus calculating the mole number of reacted propylene and the mole number of ammoxidation product in Example 1 and Comparative Example 1.

The analysis results and the molar number of supplied propylene were substituted in the following Formulas 1, 2 and 3, thus calculating conversion of propylene, selectivity and yield of acrylonitrile, which is the ammoxidation reaction product of propylene, and the calculation values were described in Table 4:

Conversion of propylene (%)=100*(mole number of ammoxidation of reacted propylene)/(mole number of supplied propylene)     Formula 1

Selectivity to acrylonitrile (%)=100*(mole number of produced acrylonitrile)/(mole number of reacted propylene)     Formula 2

Yield of acrylonitrile (%)=100*(conversion of propylene*selectivity to acrylonitrile)     Formula 3

TABLE 4

| | | Analysis results of catalysts | | Analysis results of ammoxidation product | | |
|---|---|---|---|---|---|---|
| | Preparation method | Composition and content of metal oxide | Catalyst form | Conversion of propylene (%) | Selectivity of acrylonitrile (%) | Yield of acrylonitrile (%) |
| Ex. 1 | impregnation | $Mo_{12}Bi_{1.5}Fe_3Ni_1Co_6K_1O_x$: 25 wt % | Egg-shell | 86.3 | 71.8 | 62.0 |
| Ex. 2 | impregnation | $Mo_{12}Bi_{1.5}Fe_3Ni_1Co_6K_1O_x$: 30 wt % | Egg-shell | 83.3 | 79.2 | 66.0 |
| Ex. 3 | impregnation | $Mo_{13}Bi_{1.5}Fe_3Ni_1Co_6K_1O_x$: 25 wt % | Egg-shell | 79.2 | 79.0 | 62.5 |
| Ex. 4 | impregnation | $Mo_{12.5}Bi_2Fe_3Ni_2Co_8K_{1.3}O_x$: 25 wt % | Egg-shell | 88.7 | 79.2 | 70.3 |
| Comp. Ex. 1 | Coprecipitation | $Mo_{12}Bi_{1.5}Fe_3Ni_1Co_6K_1O_x$: 50 wt % | Uniform | 56.5 | 59.6 | 33.7 |
| Comp. Ex. 2 | impregnation | $Bi_2O_3.3 \cdot MoO_3$: 25 wt % | Egg-shell | 11.3 | 50.5 | 5.7 |

Since the catalyst of Comparative Example 1 was prepared by coprecipitation and spray drying, the effective surface area (BET specific surface area) capable of participating in reactions was limited to the external surface part, and the formation of an active and amorphous phase of $CoMoO_4$ was inhibited.

Thus, the catalyst of Comparative Example 1 has low activity due to narrow effective surface area and low activity phase content, and may be easily cracked or broken due to high crystallinity. Particularly, in case the catalyst is cracked or broken by high temperature during ammoxidation of propylene, Mo, and the like may exhibit dissolution from the inside of the catalyst to the surface, and catalytic performance may be degraded.

Practically, when the catalyst of Comparative Example 1 was used for reaction, conversion of propylene was just 56.5%, and yield of acrylonitrile was just 33.7%.

Meanwhile, although the catalyst of Comparative Example 2 was prepared by impregnation, since the metal oxide comprises only Mo and Bi as metal components, effective active phases capable of participating in reactions, particularly active phase ($CoMoO_4$) could not be formed.

Practically, it was confirmed that when the catalyst of Comparative Example 2 was used for reaction, conversion of propylene and yield of acrylonitrile were even lower than Comparative Example 1.

On the contrary, since the catalysts of Examples 1 to 4 were prepared by impregnation, they have wide effective surface areas (BET specific surface areas) capable of participating in reactions, and the formation of active phase $CoMoO_4$ increased.

Thus, the catalysts of Examples 1 to 4 have high activity due to wide effective surface area and high active phase content, and may not be cracked or broken by high temperature applied during ammoxidation of propylene.

Practically, when the catalysts of Examples 1 to 4 were used for reactions, conversion of propylene was 70% or more, and yield of acrylonitrile was 60% or more.

Overall, it is estimated that a catalyst in which the composition of metal oxide meets the above explained Chemical Formula 1, and XRD main peak intensity ratio (A/B) is 1.5 or more, can remarkably improve conversion of propylene and yield of acrylonitrile during ammoxidation of propylene.

The invention claimed is:

1. An ammoxidation catalyst for propylene comprising metal oxide represented by Chemical Formula 1,
wherein a first peak having intensity of A appears in the 2θ range of 26.3±0.5°, and a second peak having intensity of B appears in the 2θ range of 28.3±0.5° in X ray diffraction analysis by CuKα, and
an intensity ratio (A/B) of the first peak to the second peak is 1.5 or more:

$$Mo_xBi_aFe_bA_cB_dC_eD_fO_y \qquad \text{Chemical Formula 1}$$

wherein in Chemical Formula 1,
A and B are different from each other, and each independently, are one or more elements of Ni, Mn, Co, Zn, Mg, Ca, and Ba,
C is one or more elements of Li, Na, K, Rb, and Cs,
D is one or more elements of Cr, W, B, Al, Ca, and V,
a to f, x, and y are respectively mole fractions of each atom or atomic group,
a is 0.1 to 7, b is 0.1 to 7, provided that the sum of a and b is 0.1 to 7,
c is 0.1 to 10, d is 0.01 to 5, e is 0.1 to 10, f is 0 to 10,
x is 11 to 14, y is a value determined by each oxidation number of Mo, Bi, Fe, A, B, C, and D.

2. The ammoxidation catalyst for propylene according to claim 1, wherein the intensity ratio (A/B) is 3.0 or more.

3. The ammoxidation catalyst for propylene according to claim 1, wherein the catalyst has BET specific surface area of 50 to 300 m²/g.

4. The ammoxidation catalyst for propylene according to claim 1, wherein a pore volume in the catalyst is 0.3 to 1.3 cm³/g.

5. The ammoxidation catalyst for propylene according to claim 1, wherein the metal oxide is represented by Chemical Formula 1-1:

$$Mo_xBi_aFe_bNi_cCo_dK_eO_y \qquad \text{Chemical Formula 1-1}$$

wherein in Chemical Formula 1-1,
a is 0.1 to 7, b is 0.1 to 7, provided that the sum of a and b is 0.1 to 7,
c is 0.1 to 10, d is 0.01 to 5, and e is 0.1 to 10,
x is 11 to 14, y is a value determined by each oxidation number of Mo, Bi, Fe, A, B, C, and D.

6. The ammoxidation catalyst for propylene according to claim 1, wherein the catalyst further comprises a silica carrier supporting the metal oxide.

7. The ammoxidation catalyst for propylene according to claim 6, wherein a weight ratio of the metal oxide to the silica carrier is 15:85 to 35:65.

8. A method for preparing the ammoxidation catalyst for propylene according to claim 1, comprising:
preparing a first precursor solution comprising a Mo precursor,
preparing a second precursor solution comprising a Fe precursor; and a precursor of one or more elements of Ni, Mn, Co, Zn, Mg, Ca, and Ba, or a second precursor solution comprising a Fe precursor; a precursor of one or more elements of Ni, Mn, Co, Zn, Mg, Ca, and Ba; and a precursor of one or more elements of Cr, W, B, Al, Ca, and V,
preparing a third precursor solution comprising a Bi precursor; a precursor of one or more elements of Ni, Mn, Co, Zn, Mg, Ca, and Ba, different from the second precursor solution; and a precursor of one or more elements of Li, Na, K, Rb, and Cs,
mixing the first to third precursor solutions such that a molar ratio of metals satisfies stoichiometric mole ratio Chemical Formula 1,
supporting the mixture of the first to third precursor solutions on a silica carrier,
drying the silica carrier on which the mixture of the first to third precursor solutions is supported, and
calcining the dried material:

$$Mo_xBi_aFe_bA_cB_dC_eD_fO_y \qquad \text{Chemical Formula 1}$$

wherein in Chemical Formula 1,
A and B are different from each other, and each independently, are one or more elements of Ni, Mn, Co, Zn, Mg, Ca, and Ba,
C is one or more elements of Li, Na, K, Rb, and Cs,
D is one or more elements of Cr, W, B, Al, Ca, and V,
a to f, x, and y are respectively mole fractions of each atom or atomic group,
a is 0.1 to 7, b is 0.1 to 7, provided that the sum of a and b is 0.1 to 7,
c is 0.1 to 10, d is 0.01 to 5, e is 0.1 to 10, f is 0 to 10,
x is 11 to 14, y is a value determined by each oxidation number of Mo, Bi, Fe, A, B, C, and D.

9. The method according to claim 8, further comprising adding citric acid, oxalic acid or a mixture thereof to the first precursor solution.

10. The method according to claim 8, wherein preparing the first precursor solution is conducted at 50 to 90° C.

11. The method according to claim 8, wherein the step of preparing a second precursor solution prepares an aqueous solution comprising water, a Fe precursor, and a Co precursor.

12. The method according to claim 8, wherein preparing the third precursor solution comprises forming a solution comprising nitric acid, a Bi precursor, a Ni precursor, and a K precursor.

13. The method according to claim 8, wherein preparing the second precursor solution and the preparing the third precursor solution are respectively conducted at 20 to 50° C.

14. The method according to claim 8, wherein mixing the first to third precursor solutions comprises:

mixing the second and third precursor solutions, and adding the mixture of the second and third precursor solutions dropwise to the first precursor solution.

15. The method according to claim 8, wherein supporting the mixture of the first to third precursor solutions on the silica carrier comprises:

first mixing the silica carrier and the first to third precursor solutions at 20 to 30° C., and second mixing the first mixture at a temperature range of 70 to 90° C.

16. The method according to claim 15, wherein the first and second mixing are respectively conducted for 1 to 3 hours.

17. The method according to claim 8, wherein drying the silica carrier in which the mixture of the first to third precursor solutions is supported is conducted at 100 to 120° C.

18. The method according to claim 8, wherein drying the silica carrier in which the mixture of the first to third precursor solutions is conducted for 5 to 12 hours.

19. The method according to claim 8, wherein calcining the dried material is conducted at 500 to 700° C.

20. A method for ammoxidation of propylene comprising the step of reacting propylene and ammonia in the presence of the catalyst of claim 1, in a reactor.

* * * * *